United States Patent
Franklin et al.

(10) Patent No.: US 8,801,597 B2
(45) Date of Patent: Aug. 12, 2014

(54) IMPLANTABLE ACCESS PORT WITH MESH ATTACHMENT RIVETS

(75) Inventors: Ethan Franklin, Goleta, CA (US); Dustin Leslie, Santa Barbara, CA (US); Kristopher Turner, Santa Barbara, CA (US); Vernon Vincent, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 61 days.

(21) Appl. No.: 13/218,300

(22) Filed: Aug. 25, 2011

(65) Prior Publication Data

US 2013/0053629 A1    Feb. 28, 2013

(51) Int. Cl.
*A61F 2/00* (2006.01)
*A61F 5/00* (2006.01)

(52) U.S. Cl.
CPC .................................. *A61F 5/0056* (2013.01)
USPC ...................... 600/37; 604/288.01

(58) Field of Classification Search
USPC ........ 600/37, 29–31; 604/8–10, 93, 174–175, 604/891.1, 909, 93.01, 288.01–288.04, 502
See application file for complete search history.

(56) References Cited

U.S. PATENT DOCUMENTS

| 586,113 | A | 7/1897 | Bott |
|---|---|---|---|
| 2,163,048 | A | 6/1939 | McKee |
| 2,737,954 | A | 3/1956 | Knapp |
| 3,371,352 | A | 3/1968 | Siposs et al. |
| 3,587,115 | A | 6/1971 | Shiley |
| 3,596,660 | A | 8/1971 | Melone |
| 3,667,081 | A | 6/1972 | Burger |
| 3,688,764 | A | 9/1972 | Reed |
| 3,840,018 | A | 10/1974 | Heifetz |
| 3,958,562 | A | 5/1976 | Hakim et al. |
| 3,971,376 | A | 7/1976 | Wichterle |
| 4,019,499 | A | 4/1977 | Fitzgerald |

(Continued)

FOREIGN PATENT DOCUMENTS

| CN | 1250382 | 4/2000 |
|---|---|---|
| CN | 1367670 | 9/2002 |

(Continued)

OTHER PUBLICATIONS

Helioscopie Product Insert for Heliogast, pp. 1-11 (undated).

(Continued)

*Primary Examiner* — Charles A Marmor, II
*Assistant Examiner* — Carrie R Dorna
(74) *Attorney, Agent, or Firm* — Gordon & Jacobson, PC

(57) ABSTRACT

The present invention generally provides a gastric banding system, including an implantable access port. The access port assembly may comprise a self-sealing septum, a housing, a mesh rivet and a mesh layer. The housing may include a septum retaining portion for holding the septum in place, and a base for defining an internal fluid reservoir and further defining a rivet receiving portion and a rivet engaging member, the housing further including a tubing connector configured to connect to a tubing for the movement of fluid into and out of the internal fluid reservoir. The mesh layer may be positioned beneath the housing and may define a plurality of spaces. The mesh rivet may engage the rivet engaging member to hold the mesh rivet in place while holding the mesh layer between a base of the mesh rivet and the housing of the access port.

16 Claims, 7 Drawing Sheets

(56) References Cited

U.S. PATENT DOCUMENTS

| | | |
|---|---|---|
| 4,118,805 A | 10/1978 | Reimels |
| 4,151,835 A | 5/1979 | Showell et al. |
| 4,161,943 A | 7/1979 | Nogier |
| 4,164,943 A | 8/1979 | Hill et al. |
| 4,190,040 A | 2/1980 | Schulte |
| 4,233,992 A | 11/1980 | Bisping |
| 4,265,252 A | 5/1981 | Chubbuck et al. |
| 4,280,722 A | 7/1981 | Guptil et al. |
| 4,413,985 A | 11/1983 | Wellner et al. |
| 4,474,572 A | 10/1984 | McNaughton et al. |
| 4,502,335 A | 3/1985 | Wamstad et al. |
| 4,543,088 A | 9/1985 | Bootman et al. |
| 4,557,722 A | 12/1985 | Harris |
| 4,569,675 A | 2/1986 | Prosl et al. |
| 4,588,394 A | 5/1986 | Schulte et al. |
| 4,592,339 A | 6/1986 | Kuzmak et al. |
| 4,592,355 A | 6/1986 | Antebi |
| 4,634,427 A | 1/1987 | Hannula et al. |
| 4,655,765 A | 4/1987 | Swift |
| 4,673,394 A | 6/1987 | Fenton, Jr. et al. |
| 4,692,146 A | 9/1987 | Hilger |
| 4,696,288 A | 9/1987 | Kuzmak et al. |
| 4,704,103 A | 11/1987 | Stober et al. |
| 4,710,174 A | 12/1987 | Moden et al. |
| 4,738,657 A | 4/1988 | Hancock et al. |
| 4,767,410 A | 8/1988 | Moden et al. |
| 4,772,270 A | 9/1988 | Wiita et al. |
| 4,778,452 A | 10/1988 | Moden et al. |
| 4,781,680 A | 11/1988 | Redmond et al. |
| 4,796,641 A | 1/1989 | Mills et al. |
| 4,802,885 A | 2/1989 | Weeks et al. |
| 4,832,054 A | 5/1989 | Bark |
| 4,840,615 A | 6/1989 | Hancock et al. |
| 4,850,227 A | 7/1989 | Luettgen et al. |
| 4,858,623 A | 8/1989 | Bradshaw et al. |
| 4,861,341 A | 8/1989 | Woodburn |
| 4,881,939 A | 11/1989 | Newman |
| 4,886,501 A | 12/1989 | Johnston et al. |
| 4,902,278 A | 2/1990 | Maget et al. |
| 4,904,241 A | 2/1990 | Bark |
| 4,913,702 A | 4/1990 | Yum et al. |
| 4,915,690 A | 4/1990 | Cone et al. |
| 4,929,230 A | 5/1990 | Pfleger |
| 4,929,236 A | 5/1990 | Sampson |
| 4,966,588 A | 10/1990 | Rayman et al. |
| 4,967,755 A | 11/1990 | Pohndorf |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melsky et al. |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan et al. |
| 5,108,377 A | 4/1992 | Cone et al. |
| 5,125,408 A | 6/1992 | Basser |
| 5,133,753 A | 7/1992 | Bark et al. |
| 5,137,529 A | 8/1992 | Watson et al. |
| 5,147,483 A | 9/1992 | Melsky et al. |
| 5,152,747 A | 10/1992 | Olivier |
| 5,167,638 A | 12/1992 | Felix et al. |
| 5,185,003 A | 2/1993 | Brethauer |
| 5,203,864 A * | 4/1993 | Phillips ............ 606/151 |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber et al. |
| 5,250,026 A | 10/1993 | Ehrlich et al. |
| 5,273,537 A | 12/1993 | Haskvitz et al. |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg et al. |
| 5,337,747 A | 8/1994 | Neftel |
| 5,360,407 A | 11/1994 | Leonard et al. |
| 5,368,040 A | 11/1994 | Carney |
| 5,387,192 A | 2/1995 | Glantz et al. |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil, Jr. et al. |
| 5,540,648 A | 7/1996 | Yoon |
| 5,556,388 A | 9/1996 | Johlin, Jr. |
| 5,558,641 A | 9/1996 | Glantz et al. |
| 5,562,617 A | 10/1996 | Finch, Jr. et al. |
| 5,571,104 A | 11/1996 | Li |
| 5,575,777 A | 11/1996 | Cover et al. |
| 5,601,604 A | 2/1997 | Vincent |
| 5,637,102 A | 6/1997 | Tolkoff et al. |
| 5,653,755 A | 8/1997 | Ledergerber |
| 5,658,298 A | 8/1997 | Vincent et al. |
| 5,674,397 A | 10/1997 | Pawlak et al. |
| 5,683,447 A | 11/1997 | Bush et al. |
| 5,688,237 A | 11/1997 | Rozga et al. |
| 5,695,490 A | 12/1997 | Flaherty et al. |
| 5,716,342 A | 2/1998 | Dumbraveanu et al. |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin et al. |
| 5,814,019 A | 9/1998 | Steinbach et al. |
| 5,833,654 A | 11/1998 | Powers et al. |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen et al. |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank et al. |
| 5,932,460 A | 8/1999 | Mills et al. |
| 5,935,083 A | 8/1999 | Williams |
| 5,938,669 A | 8/1999 | Klaiber et al. |
| 5,951,512 A | 9/1999 | Dalton |
| 6,024,704 A | 2/2000 | Meador et al. |
| 6,030,369 A | 2/2000 | Engelson et al. |
| 6,039,712 A | 3/2000 | Fogarty et al. |
| 6,074,341 A | 6/2000 | Anderson et al. |
| 6,090,066 A | 7/2000 | Schnell |
| 6,098,405 A | 8/2000 | Miyata et al. |
| 6,102,678 A | 8/2000 | Peclat |
| 6,102,922 A | 8/2000 | Jakobsson et al. |
| 6,123,700 A | 9/2000 | Mills et al. |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen et al. |
| 6,221,024 B1 | 4/2001 | Miesel |
| 6,234,973 B1 | 5/2001 | Meador et al. |
| 6,258,079 B1 | 7/2001 | Burbank et al. |
| 6,264,676 B1 | 7/2001 | Gellman et al. |
| 6,270,475 B1 | 8/2001 | Bestetti et al. |
| 6,283,949 B1 | 9/2001 | Roorda |
| 6,321,124 B1 | 11/2001 | Cigaina |
| 6,349,740 B1 | 2/2002 | Cho et al. |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda et al. |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent et al. |
| 6,572,587 B2 | 6/2003 | Lerman et al. |
| 6,589,184 B2 | 7/2003 | Noren et al. |
| 6,648,849 B2 | 11/2003 | Tenhuisen et al. |
| 6,666,845 B2 | 12/2003 | Hooper et al. |
| 6,689,100 B2 | 2/2004 | Connelly et al. |

(56) References Cited

U.S. PATENT DOCUMENTS

| | | | |
|---|---|---|---|
| 6,723,053 B2 | 4/2004 | Ackerman et al. | |
| 6,733,519 B2 | 5/2004 | Lashinski et al. | |
| 6,792,309 B1 | 9/2004 | Noren | |
| 6,810,880 B1 | 11/2004 | Jennings, Jr. et al. | |
| 6,813,964 B1 | 11/2004 | Clark et al. | |
| 6,860,857 B2 | 3/2005 | Noren et al. | |
| 6,915,162 B2 | 7/2005 | Noren et al. | |
| 6,921,267 B2 | 7/2005 | van Oostrom et al. | |
| 6,929,631 B1 | 8/2005 | Brugger et al. | |
| 6,939,299 B1 | 9/2005 | Petersen et al. | |
| 6,953,444 B2 | 10/2005 | Rosenberg | |
| 6,964,204 B2 | 11/2005 | Clark et al. | |
| 6,966,875 B1 | 11/2005 | Longobardi | |
| 6,997,914 B2 | 2/2006 | Smith et al. | |
| 7,017,583 B2 | 3/2006 | Forsell | |
| 7,020,531 B1 | 3/2006 | Colliou et al. | |
| 7,056,286 B2 | 6/2006 | Ravenscroft et al. | |
| 7,063,669 B2 | 6/2006 | Brawner et al. | |
| 7,073,387 B2 | 7/2006 | Zdeblick et al. | |
| 7,082,843 B2 | 8/2006 | Clark et al. | |
| 7,131,945 B2 | 11/2006 | Fink et al. | |
| 7,144,400 B2 | 12/2006 | Byrum et al. | |
| 7,149,587 B2 | 12/2006 | Wardle et al. | |
| 7,191,007 B2 | 3/2007 | Desai et al. | |
| 7,195,774 B2 | 3/2007 | Carvalho et al. | |
| 7,223,239 B2 | 5/2007 | Schulze et al. | |
| 7,226,419 B2 | 6/2007 | Lane et al. | |
| 7,261,003 B2 | 8/2007 | McDonald et al. | |
| 7,267,645 B2 | 9/2007 | Anderson et al. | |
| 7,282,023 B2 | 10/2007 | Frering | |
| 7,311,716 B2 | 12/2007 | Byrum | |
| 7,311,717 B2 | 12/2007 | Egle | |
| 7,351,198 B2 | 4/2008 | Byrum et al. | |
| 7,351,226 B1 | 4/2008 | Herskowitz | |
| 7,351,240 B2 | 4/2008 | Hassler, Jr. et al. | |
| 7,353,747 B2 | 4/2008 | Swayze et al. | |
| 7,364,542 B2 | 4/2008 | Jambor et al. | |
| 7,367,937 B2 | 5/2008 | Jambor et al. | |
| 7,374,557 B2 | 5/2008 | Conlon et al. | |
| 7,374,565 B2 | 5/2008 | Hassler, Jr. et al. | |
| 7,390,294 B2 | 6/2008 | Hassler, Jr. | |
| 7,413,547 B1 | 8/2008 | Lichtscheidl et al. | |
| 7,416,528 B2 | 8/2008 | Crawford et al. | |
| 7,437,951 B2 | 10/2008 | McDonald et al. | |
| 7,438,718 B2 | 10/2008 | Milliman et al. | |
| 7,445,614 B2 | 11/2008 | Bunodiere et al. | |
| 7,468,038 B2 | 12/2008 | Ye et al. | |
| 7,500,944 B2 | 3/2009 | Byrum et al. | |
| 7,510,530 B2 | 3/2009 | Hashimoto et al. | |
| 7,530,943 B2 | 5/2009 | Lechner | |
| 7,553,298 B2 | 6/2009 | Hunt et al. | |
| 7,561,916 B2 | 7/2009 | Hunt et al. | |
| 7,580,746 B2 | 8/2009 | Gilkerson et al. | |
| 7,591,185 B1 | 9/2009 | Mothilal et al. | |
| 7,593,777 B2 | 9/2009 | Gerber | |
| 7,634,319 B2 | 12/2009 | Schneider et al. | |
| 7,651,483 B2 | 1/2010 | Byrum et al. | |
| 7,658,196 B2 | 2/2010 | Ferreri et al. | |
| 7,699,770 B2 | 4/2010 | Hassler, Jr. et al. | |
| 7,708,722 B2 | 5/2010 | Glenn | |
| 7,762,998 B2 | 7/2010 | Birk et al. | |
| 7,762,999 B2 | 7/2010 | Byrum | |
| 7,775,215 B2 | 8/2010 | Hassler, Jr. et al. | |
| 7,775,966 B2 | 8/2010 | Dlugos et al. | |
| 7,811,275 B2 | 10/2010 | Birk et al. | |
| 7,850,660 B2 | 12/2010 | Uth et al. | |
| 7,862,546 B2 | 1/2011 | Conlon et al. | |
| 7,879,100 B2 | 2/2011 | Denoziere | |
| 7,909,754 B2 | 3/2011 | Hassler, Jr. et al. | |
| 7,909,804 B2 | 3/2011 | Stats | |
| 8,007,474 B2 | 8/2011 | Uth et al. | |
| 2001/0052141 A1 | 12/2001 | Andersen | |
| 2002/0013545 A1 | 1/2002 | Soltanpour et al. | |
| 2002/0058969 A1 | 5/2002 | Noren et al. | |
| 2002/0087147 A1 | 7/2002 | Hooper et al. | |
| 2002/0095181 A1 | 7/2002 | Beyer | |
| 2002/0117534 A1 | 8/2002 | Green | |
| 2002/0139208 A1 | 10/2002 | Yatskov | |
| 2002/0198548 A1 | 12/2002 | Robert | |
| 2003/0045800 A1 | 3/2003 | Noren et al. | |
| 2003/0045910 A1 | 3/2003 | Sorensen et al. | |
| 2003/0073880 A1 | 4/2003 | Polsky et al. | |
| 2003/0078506 A1 | 4/2003 | Noren et al. | |
| 2003/0139690 A1 | 7/2003 | Aebli et al. | |
| 2004/0064110 A1 | 4/2004 | Forsell | |
| 2004/0065615 A1 | 4/2004 | Hooper et al. | |
| 2004/0068233 A1 | 4/2004 | DiMatteo | |
| 2004/0082908 A1 | 4/2004 | Whitehurst et al. | |
| 2004/0111050 A1 | 6/2004 | Smedley et al. | |
| 2004/0204692 A1 | 10/2004 | Eliasen | |
| 2004/0254536 A1* | 12/2004 | Conlon et al. | 604/175 |
| 2004/0254537 A1 | 12/2004 | Conlon et al. | |
| 2004/0260229 A1 | 12/2004 | Meir | |
| 2004/0260319 A1 | 12/2004 | Egle | |
| 2004/0267288 A1 | 12/2004 | Byrum et al. | |
| 2004/0267291 A1 | 12/2004 | Byrum et al. | |
| 2004/0267292 A1 | 12/2004 | Byrum et al. | |
| 2004/0267293 A1 | 12/2004 | Byrum et al. | |
| 2004/0267377 A1 | 12/2004 | Egle | |
| 2005/0010177 A1 | 1/2005 | Tsai | |
| 2005/0049578 A1 | 3/2005 | Tu et al. | |
| 2005/0070875 A1 | 3/2005 | Kulessa | |
| 2005/0070937 A1 | 3/2005 | Jambor et al. | |
| 2005/0085778 A1 | 4/2005 | Parks | |
| 2005/0092093 A1 | 5/2005 | Kang et al. | |
| 2005/0131325 A1 | 6/2005 | Chen et al. | |
| 2005/0131352 A1 | 6/2005 | Conlon et al. | |
| 2005/0131383 A1 | 6/2005 | Chen et al. | |
| 2005/0148956 A1 | 7/2005 | Conlon et al. | |
| 2005/0149143 A1 | 7/2005 | Libbus et al. | |
| 2005/0209573 A1 | 9/2005 | Brugger et al. | |
| 2005/0240155 A1 | 10/2005 | Conlon | |
| 2005/0240156 A1 | 10/2005 | Conlon | |
| 2005/0267500 A1 | 12/2005 | Hassler, Jr. et al. | |
| 2005/0277899 A1 | 12/2005 | Conlon et al. | |
| 2005/0283041 A1 | 12/2005 | Egle | |
| 2005/0283118 A1 | 12/2005 | Uth et al. | |
| 2005/0283119 A1 | 12/2005 | Uth et al. | |
| 2006/0074439 A1 | 4/2006 | Garner et al. | |
| 2006/0122578 A1 | 6/2006 | Lord et al. | |
| 2006/0161186 A1 | 7/2006 | Hassler, Jr. et al. | |
| 2006/0173423 A1 | 8/2006 | Conlon | |
| 2006/0173424 A1 | 8/2006 | Conlon | |
| 2006/0178647 A1 | 8/2006 | Stats | |
| 2006/0178648 A1 | 8/2006 | Barron et al. | |
| 2006/0184141 A1 | 8/2006 | Smith et al. | |
| 2006/0189887 A1 | 8/2006 | Hassler, Jr. et al. | |
| 2006/0189888 A1 | 8/2006 | Hassler, Jr. et al. | |
| 2006/0190039 A1 | 8/2006 | Birk et al. | |
| 2006/0199997 A1 | 9/2006 | Hassler, Jr. et al. | |
| 2006/0211912 A1 | 9/2006 | Dlugos et al. | |
| 2006/0211913 A1 | 9/2006 | Dlugos et al. | |
| 2006/0211914 A1 | 9/2006 | Hassler, Jr. et al. | |
| 2006/0217668 A1 | 9/2006 | Schulze et al. | |
| 2006/0217673 A1* | 9/2006 | Schulze et al. | 604/288.02 |
| 2006/0235445 A1 | 10/2006 | Birk et al. | |
| 2006/0235448 A1 | 10/2006 | Roslin et al. | |
| 2006/0247539 A1 | 11/2006 | Schugt et al. | |
| 2006/0266128 A1 | 11/2006 | Clark et al. | |
| 2006/0293625 A1 | 12/2006 | Hunt et al. | |
| 2006/0293626 A1 | 12/2006 | Byrum et al. | |
| 2006/0293627 A1 | 12/2006 | Byrum et al. | |
| 2006/0293628 A1 | 12/2006 | Hunt et al. | |
| 2007/0010790 A1 | 1/2007 | Byrum et al. | |
| 2007/0015954 A1 | 1/2007 | Dlugos | |
| 2007/0015955 A1 | 1/2007 | Tsonton | |
| 2007/0016231 A1 | 1/2007 | Jambor et al. | |
| 2007/0027356 A1 | 2/2007 | Ortiz | |
| 2007/0038255 A1 | 2/2007 | Kieval et al. | |
| 2007/0060959 A1 | 3/2007 | Salo et al. | |
| 2007/0073250 A1 | 3/2007 | Schneiter | |
| 2007/0078391 A1 | 4/2007 | Wortley et al. | |
| 2007/0088336 A1 | 4/2007 | Dalton | |
| 2007/0088391 A1 | 4/2007 | McAlexander et al. | |

(56) References Cited

U.S. PATENT DOCUMENTS

| | | |
|---|---|---|
| 2007/0129765 A1 | 6/2007 | Gilkerson et al. |
| 2007/0135758 A1 | 6/2007 | Childers et al. |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos et al. |
| 2007/0173685 A1 | 7/2007 | Jambor et al. |
| 2007/0185462 A1 | 8/2007 | Byrum |
| 2007/0191717 A1 | 8/2007 | Rosen et al. |
| 2007/0205384 A1 | 9/2007 | Kurosawa |
| 2007/0208313 A1 | 9/2007 | Conlon et al. |
| 2007/0213837 A1 | 9/2007 | Ferreri et al. |
| 2007/0219510 A1 | 9/2007 | Zinn et al. |
| 2007/0235083 A1 | 10/2007 | Dlugos |
| 2007/0250086 A1 | 10/2007 | Wiley et al. |
| 2007/0255165 A1 | 11/2007 | Uesugi et al. |
| 2007/0255234 A1 | 11/2007 | Haase et al. |
| 2007/0265666 A1 | 11/2007 | Roberts et al. |
| 2007/0282196 A1 | 12/2007 | Birk et al. |
| 2007/0293829 A1 | 12/2007 | Conlon et al. |
| 2008/0009680 A1 | 1/2008 | Hassler, Jr. |
| 2008/0015406 A1 | 1/2008 | Dlugos et al. |
| 2008/0039772 A1 | 2/2008 | Chantriaux et al. |
| 2008/0058632 A1 | 3/2008 | Tai et al. |
| 2008/0097496 A1 | 4/2008 | Chang et al. |
| 2008/0114308 A1 | 5/2008 | di Palma et al. |
| 2008/0119798 A1 | 5/2008 | Chantriaux et al. |
| 2008/0132922 A1 | 6/2008 | Buevich |
| 2008/0243093 A1 | 10/2008 | Kalpin et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0281412 A1 | 11/2008 | Smith et al. |
| 2008/0287969 A1 | 11/2008 | Tsonton et al. |
| 2008/0287974 A1 | 11/2008 | Widenhouse et al. |
| 2008/0312553 A1 | 12/2008 | Timmons |
| 2008/0319435 A1 | 12/2008 | Rioux et al. |
| 2009/0018608 A1 | 1/2009 | Schwartz et al. |
| 2009/0048524 A1 | 2/2009 | Wildau et al. |
| 2009/0054914 A1 | 2/2009 | Lechner |
| 2009/0062825 A1 | 3/2009 | Pool et al. |
| 2009/0071258 A1 | 3/2009 | Kouda et al. |
| 2009/0076466 A1 | 3/2009 | Quebbemann et al. |
| 2009/0082757 A1 | 3/2009 | Rogers et al. |
| 2009/0082793 A1 | 3/2009 | Birk |
| 2009/0093768 A1 | 4/2009 | Conlon et al. |
| 2009/0099538 A1 | 4/2009 | Paganon |
| 2009/0105735 A1 | 4/2009 | Stam et al. |
| 2009/0112308 A1 | 4/2009 | Kassem |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0221974 A1 | 9/2009 | Paganon |
| 2009/0222031 A1 | 9/2009 | Axelsson |
| 2009/0222065 A1 | 9/2009 | Dlugos, Jr. et al. |
| 2009/0227862 A1 | 9/2009 | Smith et al. |
| 2009/0228028 A1 | 9/2009 | Coe et al. |
| 2009/0228072 A1 | 9/2009 | Coe et al. |
| 2009/0248125 A1 | 10/2009 | Brostrom |
| 2009/0248126 A1 | 10/2009 | Nippoldt et al. |
| 2009/0254052 A1 | 10/2009 | Birk et al. |
| 2009/0259190 A1 | 10/2009 | Birk et al. |
| 2009/0259191 A1 | 10/2009 | Birk et al. |
| 2009/0259231 A1 | 10/2009 | Birk et al. |
| 2009/0264901 A1 | 10/2009 | Franklin et al. |
| 2009/0270904 A1 | 10/2009 | Birk et al. |
| 2009/0299216 A1 | 12/2009 | Chen et al. |
| 2009/0299672 A1 | 12/2009 | Zhang et al. |
| 2009/0306462 A1 | 12/2009 | Lechner |
| 2009/0308169 A1 | 12/2009 | Mothilal et al. |
| 2010/0087843 A1 | 4/2010 | Bertolote et al. |
| 2010/0100079 A1 | 4/2010 | Berkcan et al. |
| 2010/0114149 A1 | 5/2010 | Albrecht et al. |
| 2010/0130941 A1 | 5/2010 | Conlon et al. |
| 2010/0152532 A1 | 6/2010 | Marcotte |
| 2010/0191271 A1 | 7/2010 | Lau et al. |
| 2010/0211085 A1 | 8/2010 | Uth et al. |
| 2010/0217198 A1 | 8/2010 | Franklin et al. |
| 2010/0217199 A1 | 8/2010 | Uth et al. |
| 2010/0217200 A1 | 8/2010 | Uth et al. |
| 2010/0228080 A1 | 9/2010 | Tavori et al. |
| 2010/0234808 A1 | 9/2010 | Uth et al. |
| 2011/0035008 A1 | 2/2011 | Williams |
| 2011/0054407 A1 | 3/2011 | Olroyd et al. |
| 2011/0082426 A1 | 4/2011 | Conlon et al. |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |
| WO | WO 96/40357 | 12/1996 |
| WO | WO 97/01370 | 1/1997 |
| WO | WO 99/20338 | 4/1999 |
| WO | WO 99/26543 | 6/1999 |
| WO | WO 99/34859 | 7/1999 |
| WO | WO 00/15158 | 3/2000 |
| WO | WO 00/33901 | 6/2000 |

(56) References Cited

FOREIGN PATENT DOCUMENTS

| WO | WO 01/10359 | 2/2001 |
|----|-------------|--------|
| WO | WO 01/49245 | 7/2001 |
| WO | WO 01/80926 | 11/2001 |
| WO | WO 01/95813 | 12/2001 |
| WO | WO 02/10667 | 2/2002 |
| WO | WO 02/074381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

OTHER PUBLICATIONS

Autumn K. et al.; "Evidence of Van Der Waals Adhesion in Gecko Setae"; PNAS; vol. 99; No. 19; pp. 12252-12256; Sep. 17, 2012.

Geim AK. et al.; "Microfabricated Adhesive Mimicking Gecko Foot-Hair"; Nature Materials Abstract only; vol. 2; No. 7; 2003.

Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.

Yurdumakan B., et al.; "Synthetic Gecko Foot-Hairs from Multiwalled Carbon Nanotubes"; The Royal Society of Chemistry; p. 3799-3801; 2005.

http://en/wikipedia.org/Injection_Molding.

\* cited by examiner

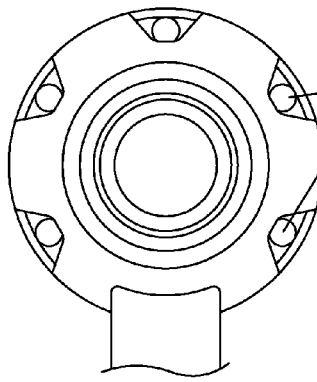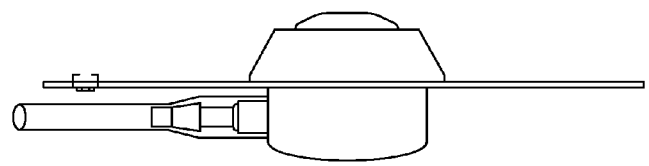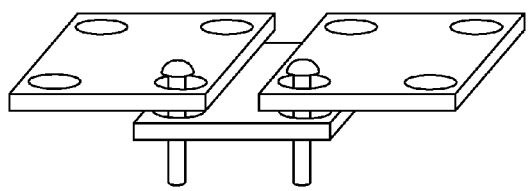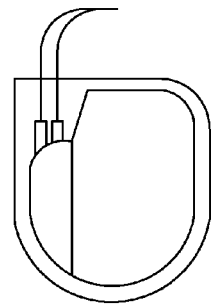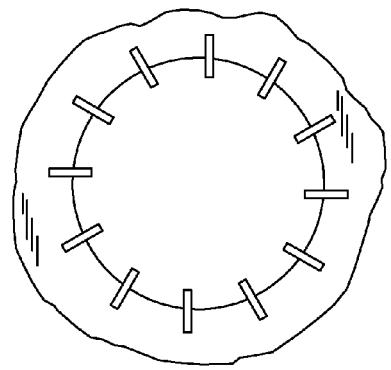
FIG. 1A
*(PRIOR ART)*
FIG. 1B
*(PRIOR ART)*
FIG. 1C
*(PRIOR ART)*
FIG. 1D
*(PRIOR ART)*
FIG. 1E
*(PRIOR ART)*

IMPLANTABLE ACCESS PORT WITH MESH ATTACHMENT RIVETS

FIELD

The present invention generally relates to medical systems and apparatus and uses thereof for treating obesity and/or obesity-related diseases, and more specifically, relates to an implantable subcutaneous access port.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the fundus, or cardia, or esophageal junction, of a patient's upper stomach forming a stoma that restricts the food's passage into a lower portion of the stomach. When the stoma is of an appropriate size that is restricted by a gastric band, the food held in the upper portion of the stomach may provide a feeling of satiety or fullness that discourages overeating. Unlike gastric bypass procedures, gastric band apparatus are reversible and require no permanent modification to the gastrointestinal tract. An example of a gastric banding system is disclosed in Roslin, et al., U.S. Patent Pub. No. 2006/0235448, the entire disclosure of which is incorporated herein by this specific reference.

Existing gastric bands periodically require adjustments to maintain an effective constriction about the stomach, to account for changes in the stomach tissue, reduction of fat or other factors causing movement and/or size change of the stomach. Some attempts have been made to allow for such adjustment of gastric bands. For example, hydraulic gastric bands utilize a fluid such as saline to fill an inflatable portion of the gastric band using a subcutaneous injection access port. Adjustments to the amount of inflation may be made by injecting or extracting the fluid through the patient's skin into or out of the injection access port, which then directs the fluid into or out of the inflatable portion of the gastric band.

Current access ports are typically configured to include a flat-surfaced septum, a rigid housing, and a substantially flat base. The housing forms a rim around the septum to expose a circular surface area of the septum. One of the main features of the access port is the port attachment and/or integration with the patient's body. The port fixation must be able to handle the load associated with locating the injection site (e.g., via palpation). Moreover, when the needle punctures the septum for the adjustment of the fluid levels within the gastric band, the port fixation must hold under the needle insertion and removal forces. While the access port may be fixated to the body of the patient in one of many ways, among the most conventional is suturing the access port to the body tissue via suture holes located on the access port, for example, as illustrated in FIG. 1A. However, solely suturing the access port to the patient's body might not be optimal in some patients. Alternatively and/or in addition, an implantable mesh may be used. The mesh is usually attached or sutured onto the access port, allowing the body tissues to ingrow around the mesh geometry.

Some attempts have been made to improve the fixation of the access port to the body of the patient. For example, Tal-larida, et al., U.S. Pat. No. 5,906,596 describes an access port with an attached mesh sandwiched between the base and top as shown in FIG. 1B, but does not describe any usage of a mesh rivet.

Williams, U.S. Pat. Pub. No. 20110035008 describes anchoring a mesh to bone as shown in FIG. 1C, but does not describe the use of a mesh rivet for attaching a mesh to an access port.

Buevich, et al., U.S. Pat. Pub. No. 20080132922 describes a fixation method using mesh to a medical device as shown in FIG. 1D. However, Buevich fails to mention the use of mesh rivets.

Green, et al., U.S. Pat. Pub. No. 20020117534 describes mesh and tissue attachments as shown in FIG. 1E. However, Green does not describe any details related to the attachment of the mesh to medical devices.

Chen, et al., U.S. Pat. Pub. No. 20050131383 describes the use of mesh with respect to injection sites as shown in FIG. 1F, but does not describe any methods of attaching the mesh.

Denoziere, et al., U.S. Pat. No. 7,879,100 describes the attachment of mesh to medical devices by molding the mesh into the medical device as shown in FIG. 1G. However, Denoziere attaches the mesh to the medical device without the use of rivets.

The access ports currently on the market and those described above suffer from known drawbacks, including cost, complexity, and effectiveness. Accordingly, it is desirable to develop a gastric banding system, and an implantable access port designed to remedy the deficiencies of access ports currently on the market.

SUMMARY

Generally described herein is a gastric banding system, including an implantable access port configured to receive and engage a mesh rivet, which is in turn, configured to penetrate a mesh layer and hold the mesh layer in place.

The access port includes a housing defining an internal fluid reservoir. The access port may have an anterior side and a posterior side, the anterior side being the side of the housing facing the patient's outer skin layer, and the posterior side being the opposite side of the housing, facing away from the patient's outer skin layer. The outer surface of the anterior side of the housing may be made entirely from a needle-penetrable and self-sealing material. And at least a portion of the posterior side of the housing may be made from a needle-resistant material. The needle penetrable and self-sealing material of the anterior side preferably comprises a pliant material, to provide a degree of compliance for the housing. In addition, on the posterior side of the housing, designated areas (e.g., a slot having an engaging member) may be configured to receive and engage or hold a mesh rivet in place.

The mesh rivet may comprise a head for insertion into a designated area and contacting the engaging member to hold the mesh rivet in place. For example, the mesh rivet may "snap" into place and engage the engaging member when the mesh rivet is inserted beyond a certain portion of the slot. The mesh rivet may have a body portion dimensioned to fit through a hole in a mesh layer and conclude with a flat base dimensioned to be larger than (and thus unable to fit through) the hole in the mesh layer. In this manner, the mesh rivet may hold the mesh layer between an exterior of the housing of the access port and the flat base.

The mesh layer, being substantially held in place, may be capable of integrating with the local body tissue of the patient. The mesh layer may be sutured or tacked to the patient's body. The mesh layer may have a skirt-like, sheet-like, or disk-like shape, and may extend out from the housing at a diameter larger than the diameter of the housing.

In one embodiment, a gastric banding system for the treatment of obesity comprises an adjustable gastric band including an inflatable portion, a tube having a first end connected to the inflatable portion and a second end, an access port connected to the tube, a mesh rivet and a mesh layer. The access port may include a housing defining an internal fluid reservoir and having a conduit with a fluid tight connection to the second end of the tube, the conduit permitting movement of fluid into and out of the internal fluid reservoir to thereby establish a fluid communication between the internal fluid reservoir and the inflatable portion of the adjustable gastric band. The access port also includes a needle penetrable septum positioned within and forming a top surface of the housing, a rivet receiving portion defined at an outer circumferential portion of the housing, and a rivet engaging member attached to the housing and located within the rivet receiving portion. The mesh rivet may include a head portion for inserting into the rivet receiving portion and engaging the rivet engaging member of the housing, and a base portion attached to the head portion. The mesh layer may have a plurality of openings for allowing the head portion of the mesh rivet to pass through one of the plurality of openings while not allowing the base portion of the mesh rivet to pass through one of the plurality of openings to hold the mesh layer between the base portion of the mesh rivet and the access port, the mesh layer configured to assist attachment of the access port to a patient upon implantation of the gastric banding system in the patient.

In one embodiment, an implantable access port assembly for use with a gastric band for the treatment of obesity is provided. The implantable access port assembly comprises a self-sealing septum, a housing, a mesh rivet and a mesh layer. The self-sealing septum may be configured to be penetrable by a needle. The housing may include a septum retaining portion for holding the septum in place, and a base for defining an internal fluid reservoir and further defining a rivet receiving portion and a rivet engaging member, the housing further including a tubing connector configured to connect to a tubing for the movement of fluid into and out of the internal fluid reservoir. The mesh layer may be positioned beneath the housing and may define a plurality of spaces. The mesh rivet may include a head, a body and a base, the head configured to penetrate a space of the plurality of spaces of the mesh layer and insertable into the rivet receiving portion to engage the rivet engaging member to hold the mesh rivet in place, the body for connecting the head to the base, and the base configured to have a surface area larger than the surface area of the space penetrated by the head for holding the mesh layer between the base and the housing.

In one embodiment, an implantable access port assembly for use with a gastric band for the treatment of obesity may include a septum, a housing, a mesh layer and a mesh rivet. The septum may be self-sealing and may be configured to be penetrable by a needle. The housing may include a septum retaining portion for holding the septum in place, and a base for defining an internal fluid reservoir and further defining a rivet locking portion along an outer circumferential portion of the housing having a rivet locking member residing within the rivet locking portion, the housing further including a tubing connector configured to connect to a tubing for the movement of fluid into and out of the internal fluid reservoir. The mesh layer may have criss-crossing wires defining a plurality of spaces and be positioned beneath the housing. And the mesh rivet may include a head, a body and a base. The head may be configured to penetrate a space of the plurality of spaces of the mesh layer and insertable into the rivet locking portion to engage the rivet locking member to hold the head in place inside the rivet locking portion, the body for connecting the head to the base, and the base located outside of the rivet locking portion and configured to have a surface area larger than the surface area of the space penetrated by the head for holding the mesh layer between the base and the housing.

BRIEF DESCRIPTION OF THE DRAWINGS

The exemplary embodiments of the present invention will be described in conjunction with the accompanying drawing FIGS. in which like numerals denote like elements.

FIG. 1A illustrates a prior art system.
FIG. 1B illustrates a prior art system.
FIG. 1C illustrates a prior art system.
FIG. 1D illustrates a prior art system.
FIG. 1E illustrates a prior art system.

DETAILED DESCRIPTION

The present invention described herein relates to a gastric banding system, including an implantable access port. The implantable access port may be used to supply fluid to and remove fluid from an inflatable bladder.

Figure 1F:
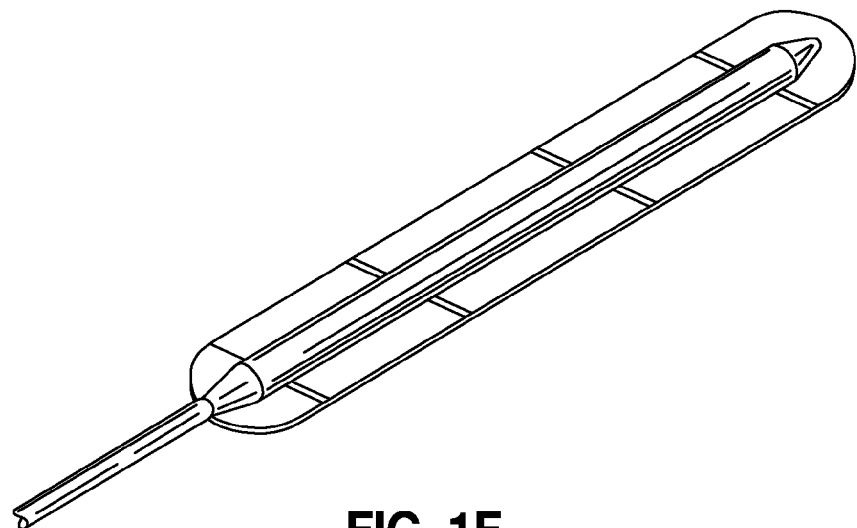
FIG. 1F illustrates a prior art system.
Figure 1G:
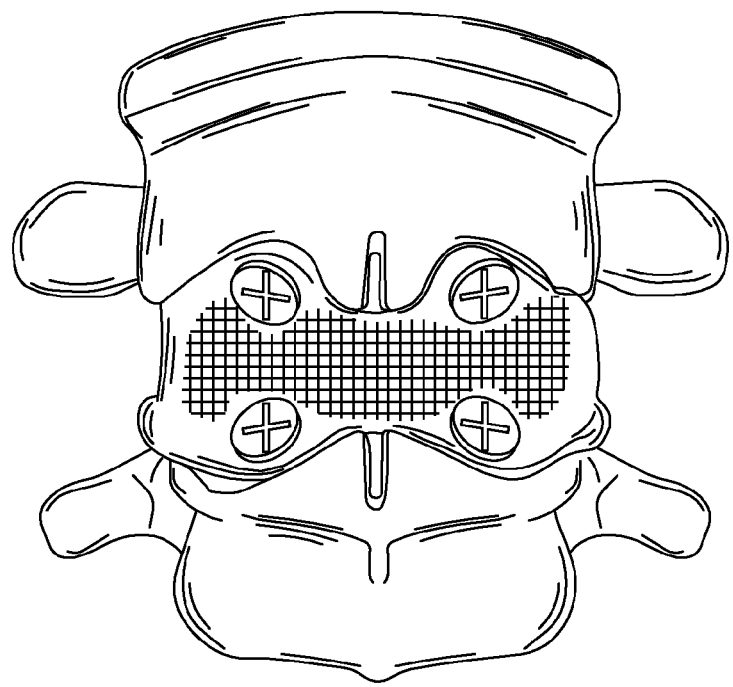
FIG. 1G illustrates a prior art system.
Figure 2:
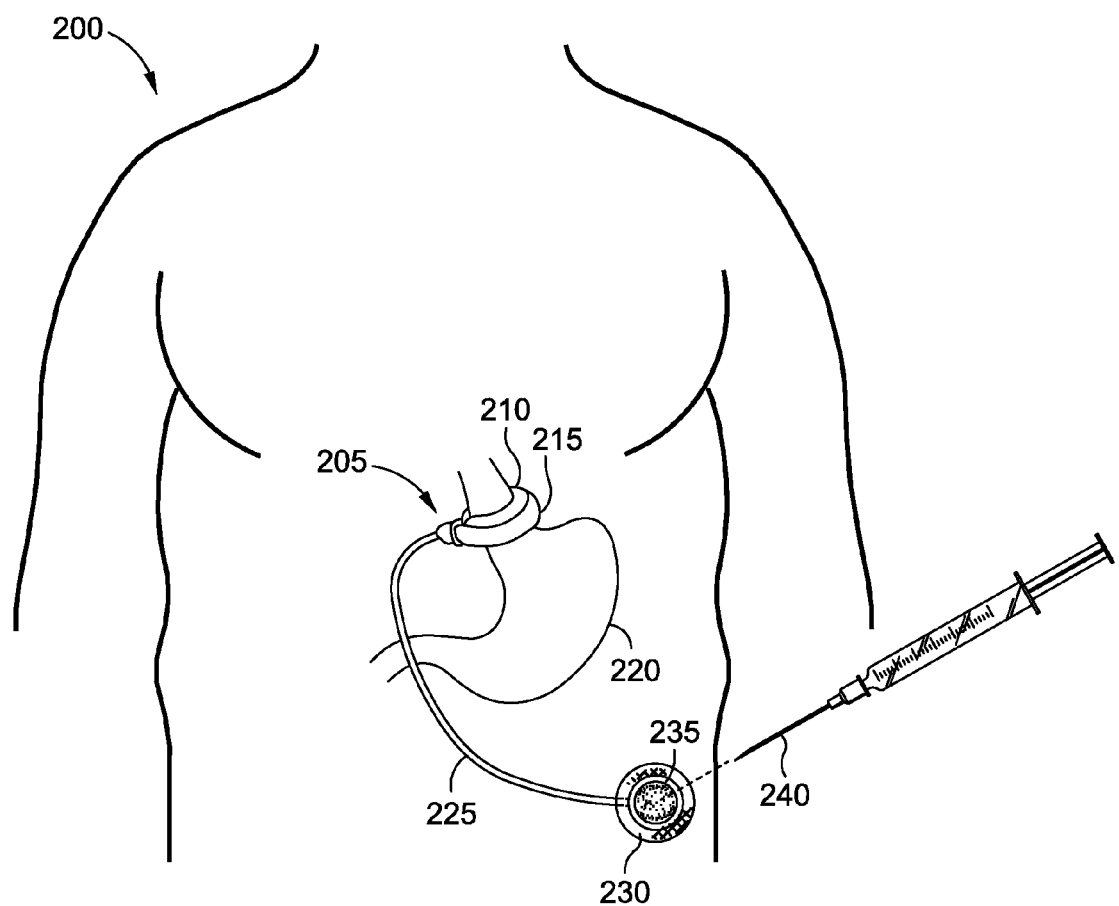
FIG. 2 illustrates a perspective view of an implanted gastric banding system according to an embodiment of the present invention.

FIG. 2 illustrates a gastric banding system 205 comprising a gastric band 215, an access port 230, and a connecting tube 225. The access port 230 may also be referred to as an injection port and the connecting tube 225 may also be referred to as a catheter. The gastric band 215 may include a lumen, an inflatable portion, or inflatable bladder 210, which is capable of being filled with fluid. The connecting tube 225 couples the inflatable bladder 210 to the access port 230 and supplies fluid to the inflatable bladder 210.

The gastric band 215 forms a loop around a portion of a stomach 220 of an individual or patient 200. The portion of the stomach 220 receiving the gastric band 215 may comprise the cardia, the fundus, or the esophageal junction of the stomach 220. The loop constricts a portion of the stomach 220 to form a stoma, which restricts the flow of food entering the lower portion of the stomach 220 when the individual 200 eats. The restricted flow of food promotes a more rapid production of satiety signals during times of food consumption than are normally produced without the restricted flow of food. The increased satiety signals may cause the individual 200 to feel full more quickly, thereby causing the individual 200 to reduce food intake. In turn, the reduced food intake may cause the individual 200 to lose weight over time.

A variable degree of constriction applied by the gastric band 215 to the stomach 220 is preferred because the biological characteristics of the stomach 220 of an individual 200 may vary over time. For example, the stomach 220 may increase or decrease in size, requiring an appropriately larger or smaller degree of constriction. In addition, the degree of constriction may need to be varied if the individual 200 is not losing weight in response to the gastric band treatment, or if the weight loss is not at a desired level. If the individual 200 is not responding appropriately to the gastric band therapy, the gastric band 215 may need to be adjusted, to increase the degree of constriction, and thereby further decrease the flow or passage of food to the lower portion of the stomach 220. In addition, variability in the size of the gastric band 215 is preferable to accommodate the unique biological characteristics of different patients, for example, patients having a smaller or larger sized stomach 220.

To accommodate a varying degree of constriction, or varying the size of the gastric band 215, the gastric band 215 may be an adjustable gastric band, or may be a gastric band having an adjustable inner diameter. The gastric band 215 may be adjusted by adjusting (i.e., reducing or increasing) the amount of fluid in the bladder 210. The bladder 210 may extend around the portion of the stomach 220 to be constricted, and may have a variable size, functioning as an inflatable cuff placed around the stomach 220. An increased bladder 210 size may increase the degree of constriction applied to the stomach 220, and a decreased bladder 210 size may decrease the degree of constriction. Accordingly, an increased amount of fluid in the bladder 210 may increase the degree of constriction, and a decreased amount of fluid in the bladder 210 may decrease the degree of constriction.

The amount of fluid in the bladder 210 may be controlled via an access port 230. The access port 230 is preferably positioned subcutaneously within the body of the individual 200 and is preferably secured to a firm layer of tissue, for example, the muscle wall of the individual 200. A physician accesses the access port 230 through the skin of the patient to vary the amount of fluid in the gastric banding system 205. The physician inserts the syringe 240 through the skin of the patient, to penetrate a septum 235 of the access port 230 to add or remove fluid. The access port 230 is therefore preferably positioned near the surface of the skin of the individual 200 to allow a physician to more easily access the access port 230 with the syringe 240.

Figure 3:
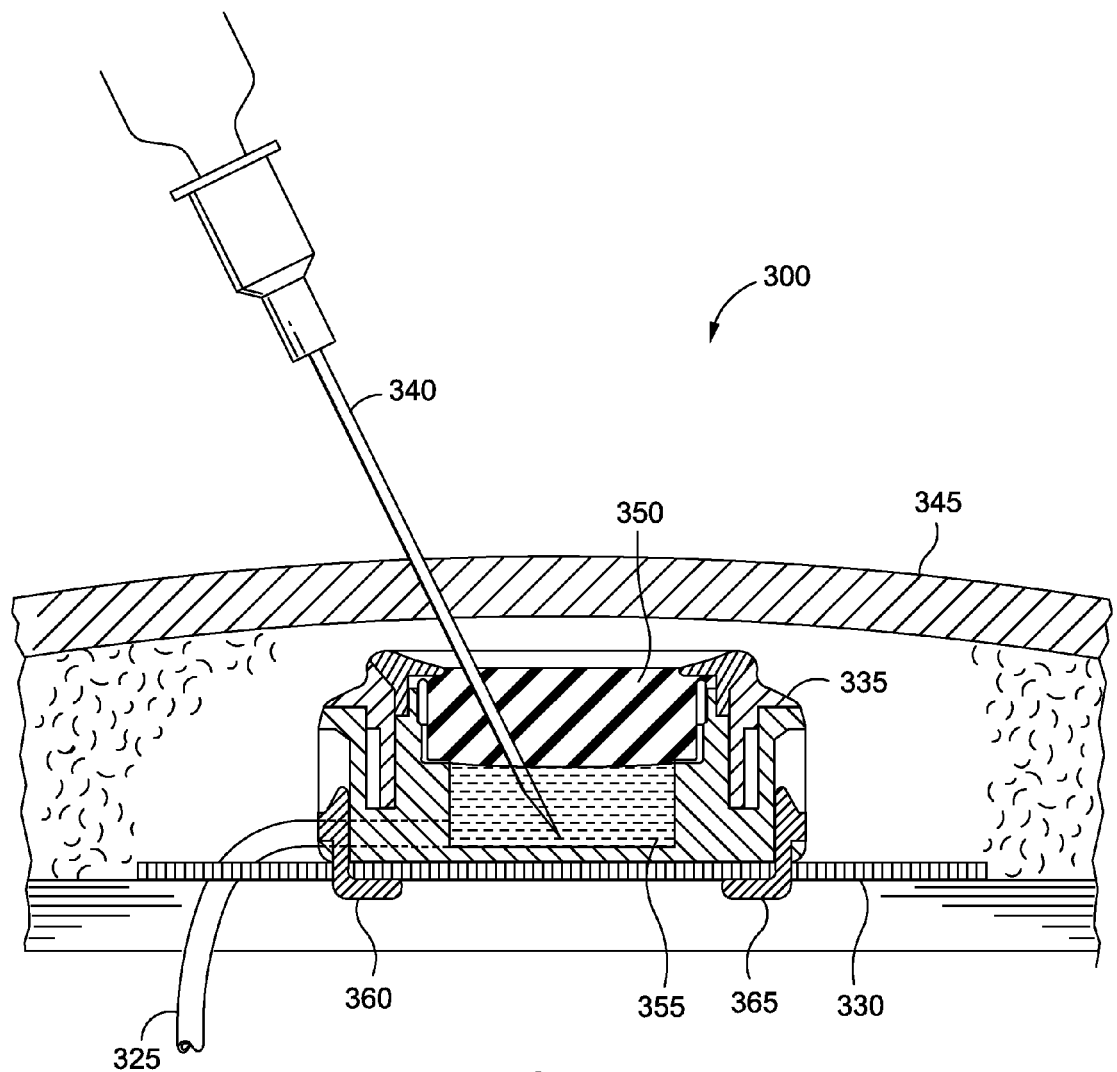
FIG. 3 illustrates a close-up, cross-sectional view of an implanted access port assembly according to an embodiment of the present invention.

FIG. 3 illustrates a needle 340 penetrating a skin 345 of a patient 300 and a septum 350, reaching a reservoir 355 of an access port 335, which enables a physician to add or remove fluid. The access port 335 of FIG. 3 is shown to be attached to a mesh layer 330 via mesh rivets 360 and 365. The mesh layer 330 may be made of a bioresorbable material, such as silk, or the like, or may be made of a non-resorbable material such as polypropylene, or the like. In addition, the mesh layer 330 may be made of a blend of both bioresorbable materials and non-resorbable materials such as a Covidien mesh, or the like. Also, the mesh layer 330 may be made of a fabric material, a rubber material, or a plastic material. The mesh layer 330 may have a microstructure or may have a circular, triangular, or other equivalent mesh structure. In one embodiment, the mesh layer 330 may comprise merely a porous material. The mesh layer 330 allows or encourages tissue ingrowth or tissue engagement after the access port 335 has been implanted in or attached to a patient. The mesh rivets 360 and 365 may be a rivet, a screw, a bolt, a wire, a nail or any other suitable connecting device or means.

The access port 335 may be the access port 230 of FIG. 2, and in the manner shown in FIG. 2, may be connected to the rest of the gastric banding system 205 via a connecting tube 325. However, the rest of the gastric banding system has been omitted in FIG. 3 for clarity.

Figure 4:
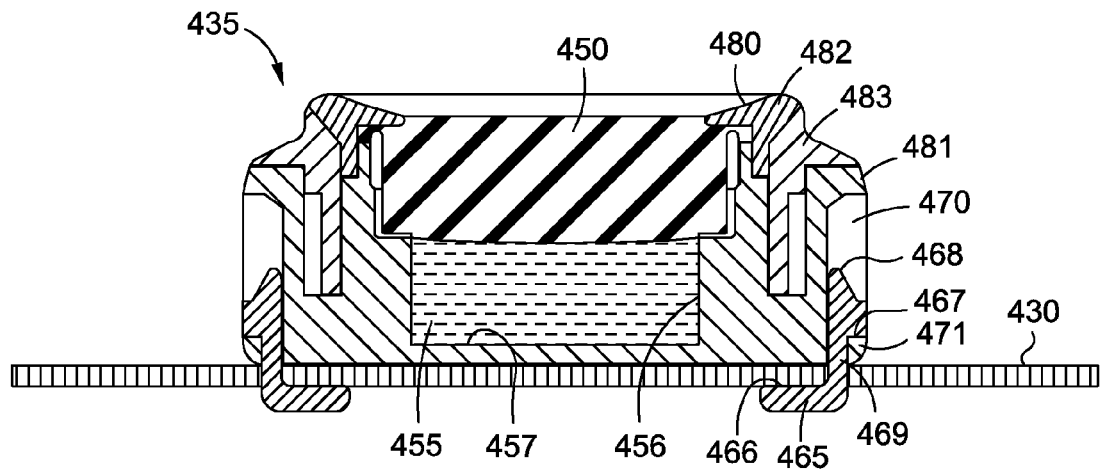
FIG. 4 illustrates a cross-sectional view of an access port assembly according to an embodiment of the present invention.

FIG. 4 further illustrates an access port 435, which in one embodiment, may be the access port 335 of FIG. 3 removed from the patient's body. Shown assembled, the access port 435 may include a housing 480 comprising a base 481 and a septum retaining portion 482 holding a septum 450 in place as shown. The housing 480 may also include a base-retainer interface 483 for structurally supporting the base 481 and the septum retaining portion 482. However, in one or more embodiments, these components may be integrated into one component housing.

The base 481 of the housing 480 may have a circumferential side wall 456 and a bottom wall 457 defining a reservoir 455 for holding fluid. The base 481, near the outside perimeter, may be configured to include a rivet receiving portion 470 (e.g., a cavity or an opening) for receiving a rivet 465. The rivet receiving portion 470 may include a rivet engaging member 471 (e.g., a protrusion or a ledge) for engaging a housing engaging member 467 on the rivet 465 to hold the rivet 465 in place when inserted into the rivet receiving portion 470. In one embodiment, the rivet engaging member 471 may be considered a rivet locking member as it may function to lock or secure the rivet 465 from exiting the rivet receiving portion 470. Similarly, the rivet receiving portion 470 may be considered a rivet locking portion as it is configured to operate with the rivet engaging member 471 to lock or secure the rivet 465 from exiting.

While omitted for clarity, the base 481 may also include a tubing connector for establishing a fluid path between the access port 435 and the inflatable portion 210 of the gastric band 215.

The rivet 465 may include a head 468, a body 469 and a base 466. The body 469 joins or is between the head 468 and the base 466. The head 468 is used to penetrate or pass through a mesh layer 430 or an opening in the mesh layer 430. In this manner, the rivet 465 holds the mesh 430 substantially in place between the base 466 of the rivet 465 and the exterior (i.e., a bottom surface) of the housing 480 of the access port 435. As shown in this embodiment, the housing 480 may comprise and/or integrate many separate components. However, the housing 480 may also be molded as substantially one-piece while still providing the rivet holding mechanism (e.g., a combination of the rivet receiving portion 470 and the rivet engaging member 471).

The various components of the access port 435 (e.g., the housing 480, the rivet 465) and the mesh 430 may be constructed out of biocompatible materials such as plastics, metals (e.g., PEEK®, titanium or stainless steel) and any combinations thereof.

Figure 5:
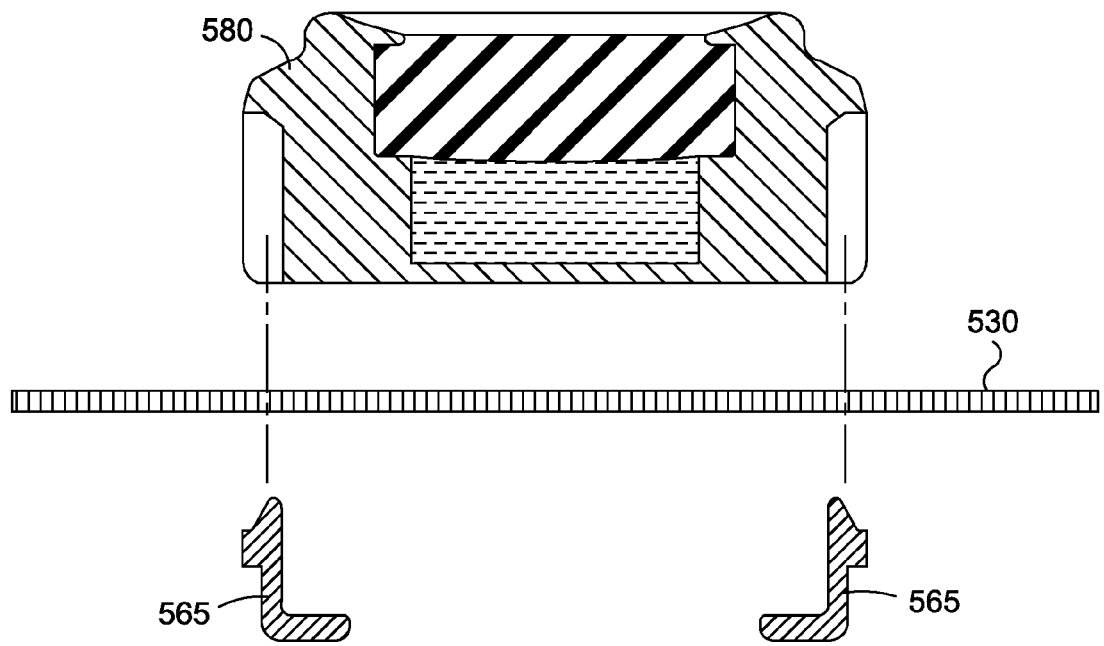
FIG. 5 illustrates an exploded simplified view of an access port assembly according to an embodiment of the present invention.

FIG. 5 is an exploded simplified view of a one-piece housing 580 of an access port along with rivets 565 and a mesh layer 530. Functionally, the housing 580 of FIG. 5 operates substantially similarly to the housing 480 of FIG. 4. The main difference is in the molding and assembly of the housing itself. However, the concept of engaging and holding the rivets 565 in place with the mesh layer 530 is still incorporated, thereby providing the same benefits as the access port 435 of FIG. 4.

While shown to be operational with a pair of rivets in FIG. 4 and FIG. 5, any number of rivets (e.g., 1, 2, 3 or 4) may be incorporated into the assembly. For example, while not shown, four rivets equally spaced apart may be utilized. Alternatively, in one embodiment, a single rivet may be utilized. For such an embodiment, it may be advantageous to move the rivet receiving portion and the rivet engagement member towards the center of the access port. Regardless, the molding used to produce the housing may be modified to accommodate both the placement of the rivet(s) and the number of rivet(s).

Figure 6A:
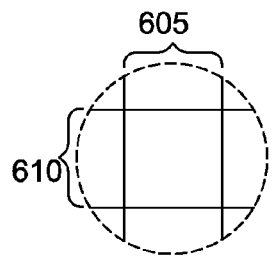
FIG. 6A illustrates a close-up view of a portion of the mesh layer of FIG. 6 according to an embodiment of the present invention.
Figure 6:
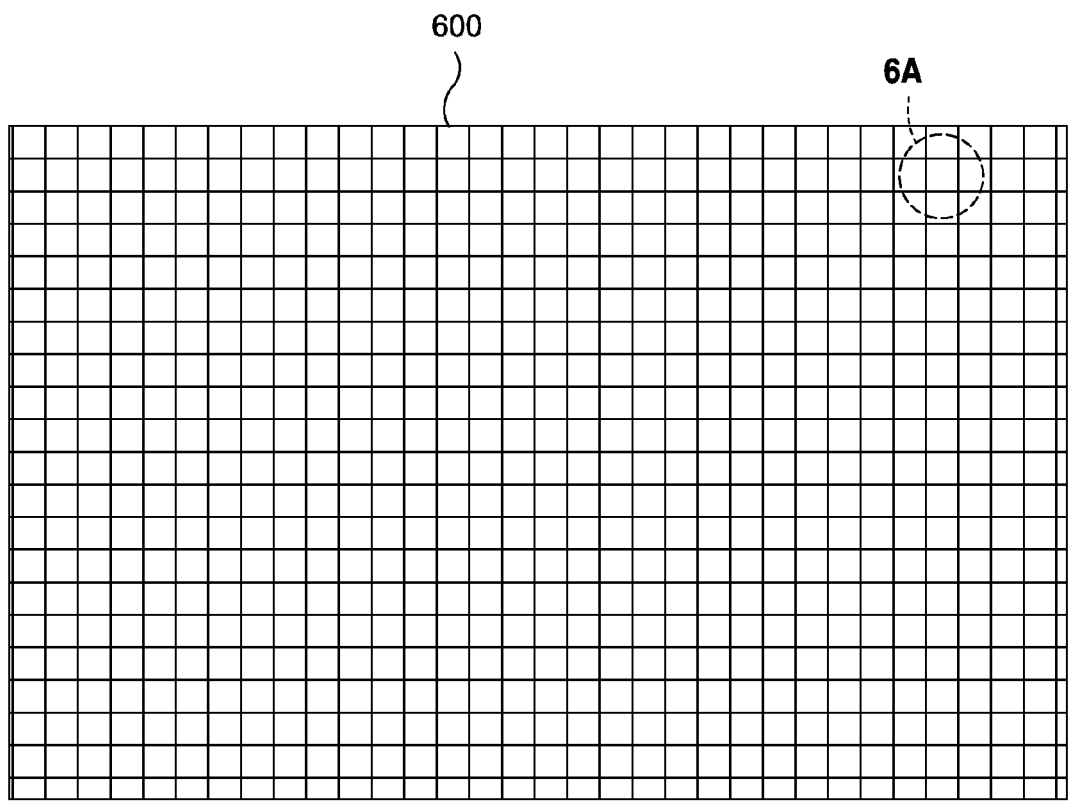
FIG. 6 illustrates a top view of a mesh layer according to an embodiment of the present invention.

FIG. 6 illustrates a top view of a mesh layer 600 which may be used in conjunction and held in place by mesh rivets (e.g., mesh rivets 365, 465 and 565). The mesh layer 600 may be formed with biocompatible material in a grid-like pattern defining a plurality of quadrilateral (e.g., diamond-shaped, square or rectangular) spaces or openings. FIG. 6A illustrates a close-up view showing a pair of wires 605 crossing a perpendicular set of wires 610 to define a square or rectangular space or opening. The mesh layer 600 may be woven to allow the bodily tissue to ingrow the spacing to provide a better integration with the body. In addition, the particular spaces or openings may be configured to allow a rivet head to pass through while ensuring that the base of a rivet does not pass through. That is, the base 466 of the rivet 465 has a length or a width or a diameter that is greater in size than a corresponding length or width or a diameter of an opening in the mesh layer 600. This configuration allows the base 466 of the rivet 465 to hold the mesh layer 600 substantially in position.

Figure 7A:
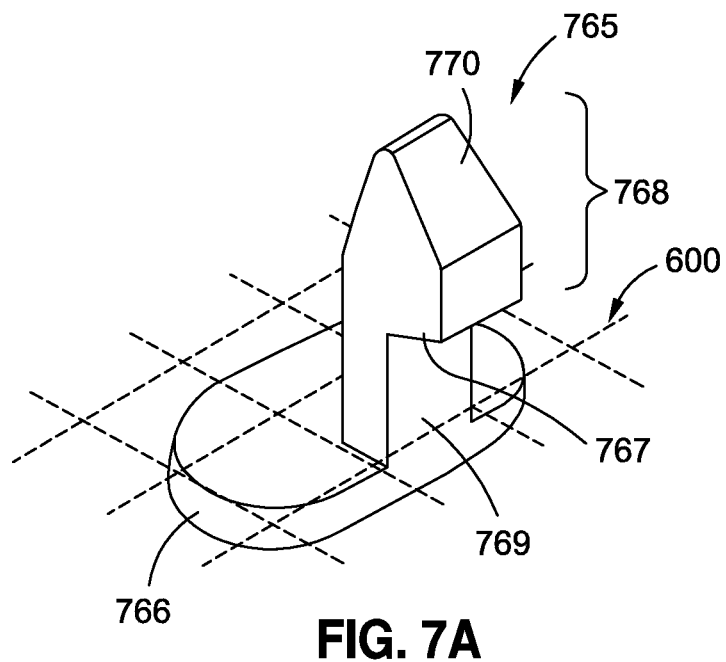
FIG. 7A illustrates a perspective view of a mesh rivet and a mesh layer according to an embodiment of the present invention.

FIG. 7A illustrates a mesh rivet 765 having a head 768, a body 769 and a base 766. As shown, the head 768 and the body 769 of the mesh rivet 765 passes through a space or opening in the mesh layer (e.g., mesh layer 600) while the base 766 is prevented from passing through the same space.

Figure 7B:
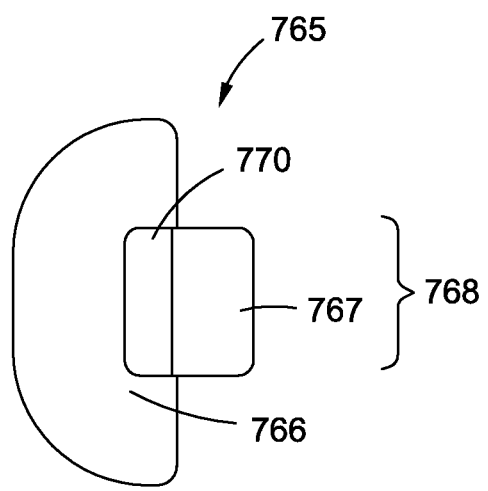
FIG. 7B illustrates a top view of the mesh rivet of FIG. 7A according to an embodiment of the present invention.

FIG. 7B illustrates a top view of the head 768 and further illustrates how a housing engagement member 767 extends beyond the base 766. Referring back to FIG. 7A, the surface area of the base 766 may be designed to be larger than the surface area of a space or opening in the mesh layer 600. In one embodiment, the surface area of the base 766 may be 1.2-2.0 times larger than the surface area of one space or opening in the mesh layer. Alternatively and/or in addition, the shape of the base 766 may be designed to be different than the shape of a space or an opening of the mesh layer 600 to prevent the base 766 from passing through the space in the mesh layer 600. For example, the base 766 of FIG. 7A is shown to be a half moon shape while the space or opening of the mesh layer 600 is substantially rectangular. However, any alternative shape may be utilized. The rivets 765 may be designed to be of minimal volume as to avoid hindering the exposure of the mesh layer to the body tissues and to avoid contributing to the bulkiness of the port.

The body 769 of the mesh rivet 765 is illustrated to be positioned at an edge of the base 766 and substantially orthogonal to the top surface of the base 766. However, other positioning is possible provided that the head 768 is allowed to pass through the mesh layer 600 to be engaged and/or held by the access port housing (e.g., housing 480 or 580).

In this embodiment, the head 768 is attached to the body 769 and may include a tapered apex 770 and a housing engagement member 767. The tapered apex 770 allows for easier entry into a rivet receiving portion (e.g., rivet receiving portion 470 of FIG. 4) while the housing engagement member 767 engages a rivet engagement member (e.g., rivet engagement member 471 of FIG. 4) and holds the head 768 in place once inserted into the rivet receiving portion. For example, once the head 768 is inserted into the rivet receiving portion such that the housing engagement member 767 is positioned above the rivet engagement member, the housing engagement member 767 protrudes over the rivet engagement member 767 and is thereby blocked from retreating out of the rivet receiving portion unless, for example, a large force is applied to pull the head 768 out of the rivet receiving portion. In one embodiment, the housing engaging member 767 may be considered a housing locking member as it is configured to engage the rivet engagement member to lock the rivet and prevent the rivet from exiting the rivet receiving portion.

In one embodiment, the body 769 may be shortened or eliminated from the mesh rivet 765 and the head 768 may be directly integrated or connected to the base 766.

The various access port embodiments described throughout this application are not limited to use in a gastric band system, or for the treatment of obesity. It is contemplated the access port may be used in various other medical applications, including other medical implantable devices, including skin expanders, or drug delivery systems.

Unless otherwise indicated, all numbers expressing quantities of ingredients, components, forces, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A gastric banding system for the treatment of obesity comprising:
   a gastric band including an inflatable portion;
   a tube having a first end connected to the inflatable portion and a second end;
   an access port including:
      a housing defining an internal fluid reservoir and having a conduit with a fluid tight connection to the second end of the tube, the conduit permitting movement of fluid into and out of the internal fluid reservoir to thereby establish a fluid communication between the internal fluid reservoir and the inflatable portion of the gastric band,
      a needle penetrable septum positioned within and forming a top surface of the housing,
      a rivet receiving portion defined at an outer circumferential portion of the housing, and
      a rivet engaging member attached to the housing and located within the rivet receiving portion;
   a mesh rivet having a head portion with a tapered insertion portion configured to fit inside the rivet receiving portion and a housing engaging member configured to contact and engage the rivet engaging member inside the rivet receiving portion of the access port to prevent the head portion of the mesh rivet from exiting the rivet receiving portion of the access port, and a base portion attached to the head portion; and
   a mesh layer having a plurality of openings for allowing the head portion of the mesh rivet to pass through one of the plurality of openings while not allowing the base portion of the mesh rivet to pass through one of the plurality of openings to hold the mesh layer between the base portion of the mesh rivet and the access port, wherein the surface area of the base portion of the mesh rivet is larger than an opening of the mesh layer, the mesh layer assisting attachment of the access port to a patient upon implantation of the gastric banding system in the patient.

2. The gastric banding system of claim 1 wherein the plurality of openings of the mesh layer not passed through by the head portion of the mesh rivet are configured to promote ingrowth of bodily tissue.

3. The gastric banding system of claim 1 further including an additional mesh rivet configured to pass through another of the plurality of openings in the mesh layer to hold the mesh layer place, and wherein the housing further includes an additional rivet receiving portion and an additional rivet engaging member for receiving and engaging the additional mesh rivet, respectively.

4. The gastric banding system according to claim 1 wherein the housing engaging member of the rivet includes a proximal surface, and the rivet engaging member of the housing includes a distal surface, and when the head portion fits inside the rivet receiving portion the proximal and distal surfaces are in contact.

5. An implantable access port assembly for use with a gastric band for the treatment of obesity, the implantable access port assembly comprising:
   a self-sealing septum configured to be penetrable by a needle;
   a housing including a septum retaining portion for holding the septum in place, and a base for defining an internal fluid reservoir and further defining a rivet receiving portion defined at an outer circumferential portion of the housing and a rivet engaging member attached to the housing and located within the rivet receiving portion, the housing further including a tubing connector configured to connect to a tubing for the movement of fluid into and out of the internal fluid reservoir;
   a mesh layer positioned beneath the housing, the mesh layer defining a plurality of openings; and
   a mesh rivet including a head, a body and a base, the head having a tapered insertion portion configured to penetrate an opening of the plurality of openings of the mesh layer and configured to fit inside the rivet receiving portion and a non-cylindrical housing engaging member configured to contact and engage the rivet engaging member of the housing inside rivet receiving portion to prevent the head from exiting the rivet receiving portion of the housing to hold the mesh rivet in place, the body for connecting the head to the base and smaller in cross-sectional area than each of the head and base, and the base configured to have a surface area larger than the surface area of the opening penetrated by the head for holding the mesh layer between the base of the rivet and the housing.

6. The implantable access port assembly of claim 5 wherein the plurality of openings of the mesh layer not penetrated by the head are configured to promote ingrowth of bodily tissue.

7. The implantable access port assembly of claim 5 further comprising an additional mesh rivet configured to penetrate another of the plurality of openings in the mesh layer to hold the mesh layer place, and wherein the housing further includes an additional rivet receiving portion and an additional rivet engaging member for receiving and engaging the additional mesh rivet, respectively.

8. The implantable access port assembly of claim 7 wherein the housing further includes a base-retainer interface for structurally supporting the base of the housing and the septum retaining portion.

9. The implantable access port assembly according to claim 5 wherein the housing engaging member of the rivet includes a proximal surface, and the rivet engaging member of the housing includes a distal surface, and when the head portion fits inside the rivet receiving portion the proximal and distal surfaces are in contact.

10. An implantable access port assembly for use with a gastric band for the treatment of obesity, the implantable access port assembly comprising:
- a self-sealing septum configured to be penetrable by a needle;
- a housing including a septum retaining portion for holding the septum in place, and a base for defining an internal fluid reservoir and further defining a rivet locking portion along an outer circumferential portion of the housing having a rivet locking member residing within the rivet locking portion, the housing further including a tubing connector configured to connect to a tubing for the movement of fluid into and out of the internal fluid reservoir;
- a mesh layer having criss-crossing wires defining a plurality of spaces, the mesh layer being positioned beneath the housing; and
- a mesh rivet including a head, a body and a base, the head having a tapered insertion portion configured to penetrate a space of the plurality of spaces of the mesh layer and insertable into the rivet locking portion and a non-cylindrical housing engaging member to engage the rivet locking member to hold the head in place inside the rivet locking portion, the body for connecting the head to the base, and the base located outside of the rivet locking portion and configured to have a surface area larger than the surface area of the space penetrated by the head for holding the mesh layer between the base of the rivet and the housing.

11. The implantable access port assembly of claim 10 wherein the housing engaging member is configured to contact and engage the rivet locking member of the housing inside rivet receiving portion to prevent the head from exiting the rivet locking portion of the housing.

12. The implantable access port assembly of claim 10 wherein the plurality of spaces of the mesh layer not penetrated by the head are configured to promote ingrowth of bodily tissue.

13. The implantable access port assembly of claim 10 further comprising an additional mesh rivet configured to penetrate another of the plurality of spaces in the mesh layer to hold the mesh layer place, and wherein the housing further includes an additional rivet locking portion and an additional rivet locking member for receiving and engaging the additional mesh rivet, respectively.

14. The implantable access port assembly of claim 10 wherein the housing further includes a base-retainer interface for structurally supporting the base of the housing and the septum retaining portion.

15. The implantable access port assembly according to claim 10 wherein the housing engaging member of the rivet includes a proximal surface, and the rivet locking member of the housing includes a distal surface, and when the head portion fits inside the rivet locking portion the proximal and distal surfaces are in contact.

16. The implantable access port assembly according to claim 10, wherein the rivet includes a body connecting the head to the base, the body being smaller in cross-sectional area than each of the head and base.

* * * * *